United States Patent
Kulkarni (10) Patent No.: US 8,775,206 B2
(45) Date of Patent: Jul. 8, 2014

(54) HEALTHCARE PRIVACY VIOLATION DETECTION AND INVESTIGATION SYSTEM AND METHOD

(71) Applicant: Amit Kulkarni, Houston, TX (US)

(72) Inventor: Amit Kulkarni, Houston, TX (US)

(*) Notice: Subject to any disclaimer, the term of this patent is extended or adjusted under 35 U.S.C. 154(b) by 0 days.

(21) Appl. No.: 13/890,205

(22) Filed: May 8, 2013

(65) Prior Publication Data

US 2013/0297346 A1   Nov. 7, 2013

Related U.S. Application Data (60) Provisional application No. 61/664,517, filed on Jun. 26, 2012, provisional application No. 61/664,570, filed on Jun. 26, 2012.

(51) Int. Cl.
*G06Q 10/00* (2012.01)
*G06F 19/00* (2011.01)

(52) U.S. Cl.
CPC .................................. *G06F 19/322* (2013.01)
USPC ................................................ 705/2; 705/3

(58) Field of Classification Search
USPC ................................ 705/2, 3; 726/25, 26, 28
See application file for complete search history.

(56) References Cited

U.S. PATENT DOCUMENTS

| | | | |
|---|---|---|---|
| 6,347,374 B1 | 2/2002 | Drake et al. | |
| 7,808,916 B1 | 10/2010 | Futamura | |
| 7,865,958 B2 * | 1/2011 | Lieblich et al. | 726/25 |
| 8,082,349 B1 * | 12/2011 | Bhargava et al. | 709/227 |
| 8,326,987 B2 * | 12/2012 | Lin | 709/225 |
| 2003/0191665 A1 | 10/2003 | Fitzgerald et al. | |
| 2004/0225627 A1 * | 11/2004 | Botros et al. | 706/16 |
| 2005/0268113 A1 * | 12/2005 | Mahone et al. | 713/189 |
| 2008/0114888 A1 * | 5/2008 | Bhatt et al. | 709/231 |
| 2008/0189136 A1 | 8/2008 | Mitgang et al. | |
| 2009/0135007 A1 | 5/2009 | Donovan et al. | |
| 2011/0125658 A1 * | 5/2011 | Lanxner et al. | 705/318 |
| 2011/0321175 A1 * | 12/2011 | Slater | 726/28 |
| 2013/0173309 A1 * | 7/2013 | Dworkin | 705/3 |
| 2013/0218592 A1 * | 8/2013 | Hashmat | 705/3 |

FOREIGN PATENT DOCUMENTS

WO   2012/074723 A1   6/2012

* cited by examiner

*Primary Examiner* — Sind Phongsvirajati
*Assistant Examiner* — Jonathan K Ng
(74) *Attorney, Agent, or Firm* — Wayne State University Law School Patent Procurement Law Clinic; Thomas D. Helmholdt (57) ABSTRACT

A method for detecting privacy violations of patient personal healthcare information (PHI) can include receiving audit logs from all systems within a healthcare facility. These audit logs are generated any time PHI is accessed. The Healthcare Privacy Violation Detection System (HPV-DS) compares these generate audit logs to prior access history of the employee or authorized user that generated the audit log. If any field in the generated audit log is different from the authorized user's prior access history, the risk of a privacy violation is assessed and a risk score is assigned. For audit logs that differ from past access history enough, an alert turned on and the audit log is flagged for administrators to review.

5 Claims, 5 Drawing Sheets

HEALTHCARE PRIVACY VIOLATION DETECTION AND INVESTIGATION SYSTEM AND METHOD

RELATED APPLICATIONS

This application is a non-provisional of U.S. provisional application No. 61/664,517, filed on Jun. 26, 2012, entitled "Healthcare Privacy Violation Detection and Investigation System and Method," and U.S. provisional application No. 61/664,570, filed on Jun. 26, 2012, entitled "Healthcare Privacy Violation Detection and Investigation System and Method", which are incorporated by reference herein in their entireties.

FIELD OF THE INVENTION

The invention relates to data processing of healthcare management and patient record management, more specifically auditing an employee's or an authorized user's access to personal healthcare information, and more particularly information security policy for privacy investigation, breach reporting, and detection system and method.

BACKGROUND

Healthcare facilities maintain massive databases containing a plethora of patient electronic medical records (EMR) and personal healthcare information (PHI). With a multitude of privileged information, the risk of inappropriate access is high. Health Insurance Portability and Accountability Act (HIPAA) and Health Information Technology for Economic and Clinical Health (HITECH) require healthcare entities to do monthly audits on their authorized users to check for any abuse of access to PHI or EMR data. To assist enforcement of these requirements, "audit logs" are generated in healthcare facilities that identify and track authorized user activity, such as who viewed, edited, printed, etc., a patient's EMR or PHI and whether that was done with a valid reason and authorized access. An automated and intelligent system that identifies abnormal usage based on prior behavior pattern recognition greatly reduces the work of administrators, e.g., Privacy and Compliance officers, who manually go through these audit reports to identify improper access.

Several systems are directed to detect certain anomalies, or abnormal activities, in data streams. Rule-based detection methods are common, as are prior usage comparison, but both are mostly directed towards finding oddities in distributed computer networks.

SUMMARY

The Healthcare Privacy Violation Detection System (HPV-DS) serves as a central point for investigative and auditing capability for HIPAA and HITECH or other compliance requirements on storing and accessing patient PHI, enabling healthcare providers to quickly and accurately monitor breaches within their systems. HPV-DS relies on past trends of authorized users in a healthcare facility to determine if an access was appropriate. Any outlier is reported, and all access that fit within normal activity are stored, but are not reported, so only the necessary occurrences are pointed out to authorities for review. The healthcare privacy violation detection system (HPV-DS) uses a healthcare facility's audit logs and non-healthcare audit logs to detect and report an authorized user's abnormal and potentially unauthorized access to a patient's personal health information (PHI).

This system collects healthcare audit logs, which are generated for every action within a healthcare facility, from various systems and departments throughout the healthcare facility. Once received, the data can be compressed and encrypted if it is desired to send the data to the Cloud through the internet. Alternatively, the data could be held at an on a premises server. When the Cloud receives the data, it is decrypted, uncompressed, parsed, and normalized. The data is normalized to ensure HPV-DS encounters uniform data, the data is not duplicated, and to discard parameters that are unnecessary.

Past access patterns and parameters are used to create a baseline for each authorized user. When an audit log contains a new user (without baseline information), HPV-DS creates an authorized user's baseline through a learning mode. Whenever HPV-DS encounters a new user, an alert is sent to the administrator (Privacy and Compliance officer), and the authorized user's baseline is built for a predetermined amount of time. During that time, the authorized user's PHI access is considered normal; at the end of this period, or when the administrator identifies the new user's patterns as normal, the HPV-DS turns to active mode for that authorized user and alerts are only triggered for pattern outliers.

Using a pattern analyzer with an anomaly detection engine, HPV-DS compares an authorized user's access data in the healthcare audit logs to the authorized user's baseline access parameters. When an audit log shows a parameter different from the baseline, a predetermined risk score for the parameter is applied to that action. The healthcare facility can assign a sliding scale of risk scores to parameters. If there are multiple parameters in the audit log that differ, a higher risk score is calculated and assigned. If a threshold score is exceeded, an alert is sent to the administrator and a ticket entry is created for detailed review. If most parameters are aligned with the baseline, a lower risk score is assigned, no alert is sent, and the record is added as more baseline data for that authorized user. HPV-DS also incorporates audit logs from non-healthcare sources that include personal authorized user information, such as addresses of the authorized user's family, family member names, work colleagues, etc. These audit logs are used to create an authorized user profile, which is incorporated to the baseline and is compared to the healthcare audit logs for alerting of any high risk access to PHI. While going through the pattern analyzer, the data can be simultaneously stored. All audit log data is kept in a database table once it has been parsed and normalized for future access to audit log information upon request.

While going through the pattern analyzer and being stored, the parsed and normalized data is checked by a patient alert rule base. This rule base is used to detect access to high profile patient's PHI or patients who are privacy conscious. If these particular patients are identified in the current audit log data, an alert is sent and a ticket entry is created for future detailed review. If these patients are not identified, then no alert is issued and no record is created.

A method for detecting privacy violations of patient personal healthcare information (PHI) access can include at least one processor for performing the steps of generating an audit log for an access to PHI by an authorized user; comparing at least one parameter of the audit log to a corresponding baseline parameter of the access to PHI by the authorized user that is considered normal; assigning a risk score to the parameter of the audit log when the parameter of the audit log differs from the corresponding baseline parameter; and adding together all of the risk scores to determine a cumulative risk score.

The method can also include weighting the cumulative risk score according to a percentage of matching parameters, and/or weighting the risk score for each parameter based on a different risk of privacy violation for a particular parameter, and/or adding audit log parameters generated by the unknown user to the new set of baseline parameters for the unknown user for a predefined time frame, and/or a learning engine routine including creating and storing a new set of baseline parameters for an unknown user when the audit log is generated by an unknown user.

A method for detecting privacy violations of patient personal healthcare information (PHI) access can include at least one processor for performing the steps of generating an audit log for an access to PHI by an authorized user; communicating with at least one system to collect the audit log; normalizing and parsing the audit log into a predefined and uniform data format; discarding parameters considered to be irrelevant to a risk of privacy violation; comparing at least one parameter of the audit log to a corresponding baseline parameter range of an access to PHI by an authorized user that is considered normal and non-healthcare authorized user information; adding a weighted risk score assigned to the corresponding baseline parameter range to a cumulative risk score for the access to PHI by the authorized user if the parameter of the audit log differs from the corresponding baseline parameter range; creating an alert and flagging the audit log when the cumulative risk score exceeds an acceptable threshold; storing the normalized and parsed audit log in a storage database; comparing the audit log to a set of patient rules; and creating the alert and flagging the audit log when at least one audit log parameter matches a corresponding parameter of the set of patient rules.

A method for detecting privacy violations of patient personal healthcare information (PHI) access can include at least one processor for performing the steps of generating an audit log when an access to PHI by an authorized user occurs; normalizing and parsing the audit log into a predefined and uniform data format; discarding parameters considered to be irrelevant to a risk of privacy violation; comparing at least one parameter of the audit log to a corresponding baseline parameter range of the authorized user and non-healthcare authorized user information; adding a weighted risk score assigned to the baseline parameter range to a cumulative risk score for the access to PHI by the authorized user, if the parameter of the audit log differs from the corresponding baseline parameter range for the authorized user; creating an alert and flagging the audit log when the cumulative risk score exceeds an acceptable threshold; storing the normalized and parsed audit log in a storage database; creating the alert and flagging the audit log when at least one audit log parameter matches a corresponding parameter of a set of patient rules; adding the audit log to the baseline parameter range for the authorized user when the cumulative risk score is under the acceptable threshold; and creating an alert when an unknown user generated the audit log and storing the audit log as the baseline parameter range for the unknown user.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DETAILED DESCRIPTION

Figure 1:
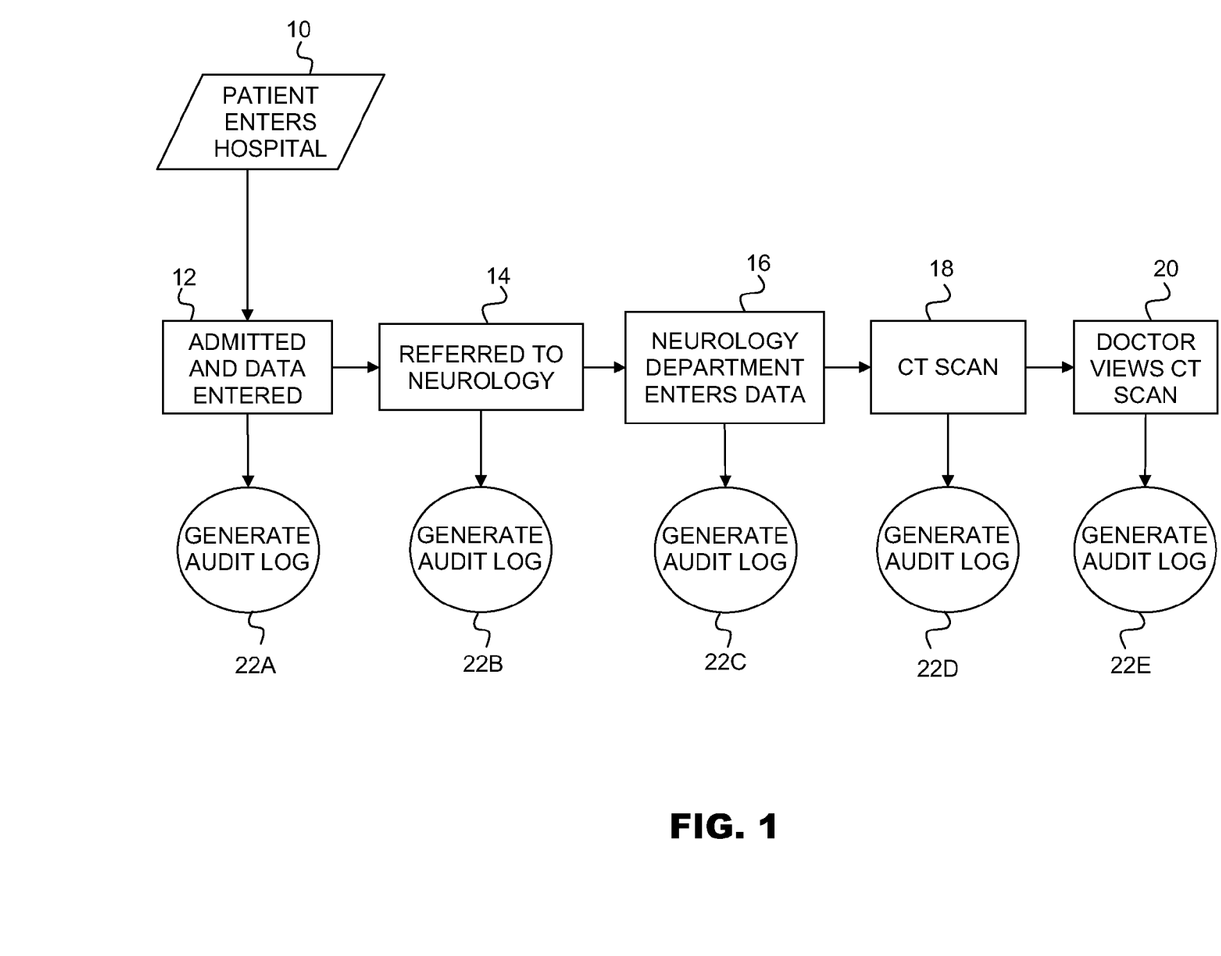
FIG. 1 is a simplified logical flow diagram of a patient through a healthcare facility.

Referring now to FIG. 1, a simplified logical flow diagram of a patient passing through a healthcare facility. Every authorized user action illustrated in boxes or steps 12-20, such as entering, altering, creating, etc., at the healthcare facility related to a patient's personal healthcare information (PHI) and/or a patient's electronic medical records (EMR) generates an audit log illustrated in boxes or steps 22A-22E. These audit logs enable the healthcare's enforcement authority, e.g., Privacy and Compliance officers, to identify and track an authorized user's activities, such as who viewed, edits, or printed a patient's PHI or EMR. Authorized users of the system include healthcare employees, contractors, and any other individual allowed to access PHI and EMR. The actions illustrated in boxes or steps 12-20 occur throughout an authorized user's day-to-day work while caring for patients. For example, when a patient enters a hospital in step 10 to receive treatment, an audit log is generated in steps 22A-22E when the patient is admitted and their data is entered in step 12, when the patient is referred to a department in step 14, when the patient's PHI is entered in a department in step 16, when the patient receives tests in step 18, when a doctor view the patient's tests in step 20, etc.

Figure 2:
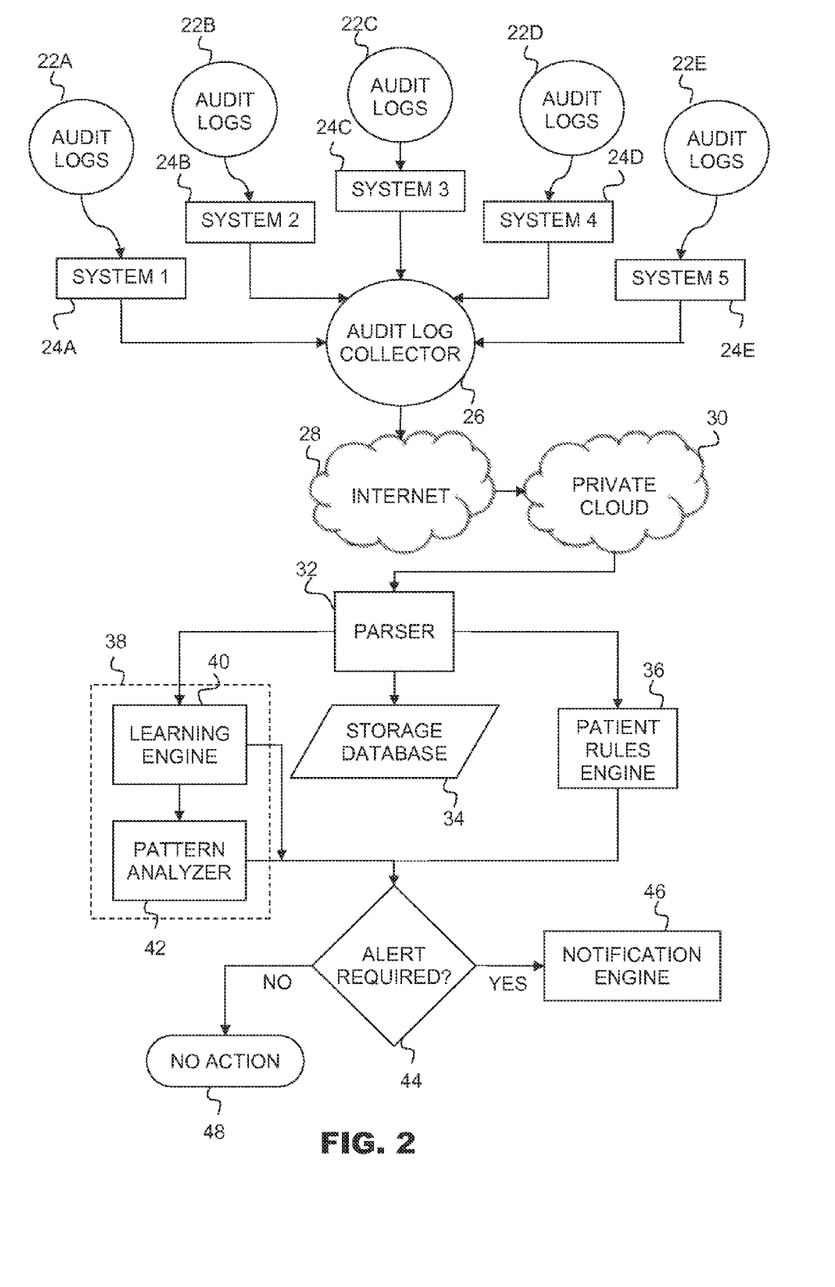
FIG. 2 is a simplified logical flow diagram overview of the healthcare privacy violation detection system (HPV-DS)

FIG. 2 shows an overview of the healthcare privacy violation detection system (HPV-DS). The audit logs of steps 22A-22E are generated throughout the entire healthcare facility and may be generated on various different healthcare software systems in steps 24A-24E in different departments, e.g., surgery, gynecology, hematology, pathology, and so on.

The audit log collector illustrated in step 26 can receives audit logs generated by all healthcare authorized users from all healthcare systems in steps 24A-24E. Certain implementations of this system as described herein can function while communicating over the internet in step 28 and with the use of a private cloud in step 30, or in the form a single physical/virtual server which may host all of the functional components, or a combination of both to provide privacy monitoring and reporting software platform that works across diverse healthcare software systems in steps 24A-24E. Once received by the audit log collector in step 26, which has the flexibility of being implemented as a virtual web/cloud or physical collector, the data can be compressed and encrypted if it is desired to be sent through the internet in step 28 to the private cloud in step 30. Alternatively, instead of steps 28 and 30, the audit log data could go directly to a server that is located on the healthcare facility's premises, if a non-cloud implementation is chosen. This is a major technical advantage of this entire system—it can completely reside on a customer's premise, or it can reside in multiple parts that can be geographically separate and still function as a highly redundant system. The portability of this system from a highly distributed to centralized computing platform is a major advantage for flexibility of deployment in large or small setups. The audit log collector of step 26 is continuously gathering audit logs once the audit logs are generated. This allows auditing to occur in real time as opposed to a batch process Alerts can be generated through the patient rules engine of step 36 and the anomaly detection engine of step 38. If it is determined that an alert is required in step 44, the notification engine of step 46 sets off the alert. If no alert is required in step 44, then no further action is taken in step 48. Authorities may be alerted via phone, email, pager, short message service (sms), text messages, etc, about privacy breaches as they happen. These alerts may also be sent to any individual desired. This system also has the ability, due to its central data storing capability, to provide access to patients and for patients to run privacy reports on themselves.

Once the private cloud of step 30 receives the audit log data, it is decrypted and uncompressed before it is accepted by the parser in step 32. Each data source of steps 24A-24E has its predefined configuration, stating the data type and the amount of data that is to be "normalized," and the rest to be discarded as "noise" or waste. For example, if the audit log data sent to the parser in step 32 has fields A, B, C, D, E, F, and G, and if the parser configuration is set to only select fields B, C, D, and G, then only those fields will be "normalized" in a uniform data format. The remaining fields, A, E, and F, are discarded as unwanted data. In another implementation, a system that is partially residing on a customer's premises that collects in step 26 the audit logs, may also include a parser in step 32 on premises, and "normalize" the data before sending it over the internet in step 28.

After the data is parsed in step 32, it is stored in step 34, sent through a patient rules engine in step 36, and sent to an anomaly detection engine in step 38, which, for purposes of explaining, breaks down into two parts, a learning engine in step 40 and a pattern analyzer in step 42. These analyses are concurrent.

The stored data in step 34 may be used to create ad hoc reports by an administrator, e.g. Privacy and Compliance officers, on request. An example of such ad hoc reports can be a report requesting authorized user activity for a certain time period, a report showing an authorized user's views of a single patient's or multiple patients' PHI or EMR. These reports can also be run across multiple systems (e.g. 24A through 24E) concurrently, whose audit logs are collected in step 26 and parsed in step 32 audit log data.

Figure 3:
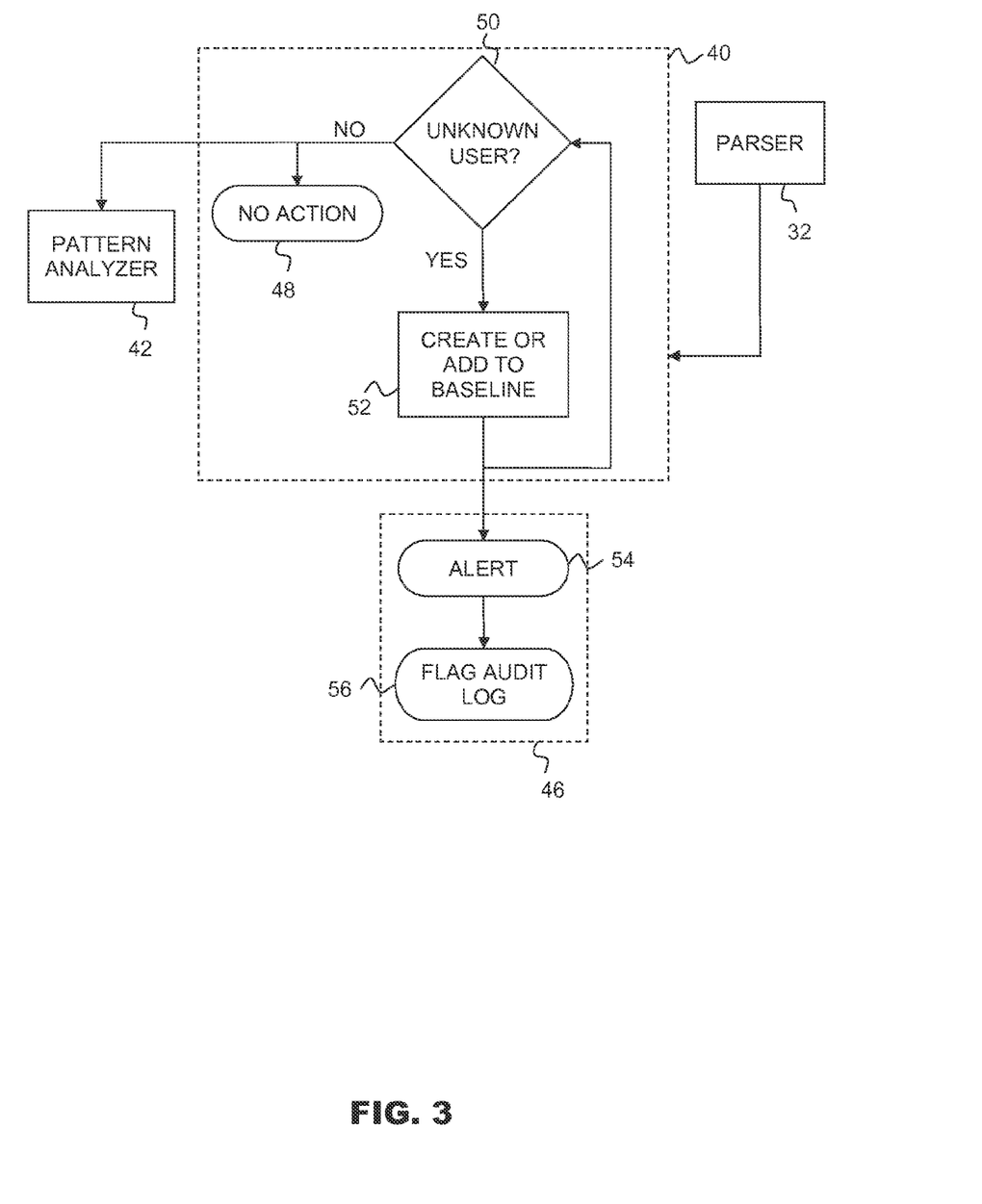
FIG. 3 is a simplified logical flow diagram of a learning engine.

FIG. 3 illustrates an example of the learning engine in step 40. The learning engine of step 40 is a part of the anomaly detection engine in step 38. After the audit logs are "normalized," the data is stored in the anomaly detection engine in step 38 to maintain patterns and parameters for all possible unique authorized users who access systems at the healthcare facility known as a "baseline." Authorized user's activity baselines are stored in the anomaly detection engine in step 38. A baseline is considered the normal level of activity by a specific authorized user. The patterns to be considered for creating a baseline may consist of previously configured criteria such as last logon time, location used from, normal patients viewed, systems the authorized user normally accesses, typical times of day authorized user uses a system, time spend on a system, patient records typically viewed, department authorized user works in, etc. many more such parameters may be added to the pattern list to suit the reporting needs of the facility. When a new or unknown user is encountered in step 50, the activity patterns for that new or unknown user are used to create or add to the baseline for that new or unknown user in step 52. Encountering an unknown user also invokes the notification engine 46, creating an alert in step 54 and flagging the data in step 56. Audit log data with activities of that new user are used to build a new baseline for that user in step 52, based on a pre-designated time frame. For that time frame, the data is assumed, or is verified, to be normal patient record access and system usage behavior by that new user. After that time frame, the new, or unknown, user is considered known, and any access or behavior by that, now authorized, user that is different from what was recorded during the designated time frame is identified and reported through the notification engine 46 by setting off an alert 54 and flagging the audit log 56. In another embodiment, encountering an unknown user in step 50 will create and/or add to their baseline in step 52, through the notification engine 46, which creates an alert in step 54 and flags in step 56, but the unknown user will only cease to be unknown until the baseline is identified as normal by an administrator. Once identified as normal, the notification engine 46 is only generated if audit log data for that authorized, previously unknown, user is different from the baseline for that authorized user.

When an audit log is flagged, it is set aside as a ticket entry, informing an administrator that it is necessary to review that particular audit log activity. Whenever the notification engine 46 is invoked, an alert is generated in step 54, the audit log is flagged in step 56. This does not have to be the case always; alerting in step 54 and flagging in step 56 can be customized by an administrator of the healthcare facility, such as creating alerts in step 54 only when a pattern exceeds a predetermined threshold in step 66, and flagging in step 56 an audit log, creating a ticket entry for administrator review, only when a new user is encountered in step 50.

Authorized user baseline data may also contain non-healthcare system information, such as Windows Active Directory or other Lightweight Directory Access Protocol stores that have identity stores that can store authorized user and domain based authentication information in an enterprise setting. Internet protocol address and Domain Name Service information of the host terminal and similar information is also received and added to the baseline analyzer to create an authorized user's profile. The work location, work shift schedule, personal or family addresses, family member names, work colleagues, and other related information of an authorized user from the Enterprise Resource Planning system, human resource system, and other similar information stores send this data to this system to create a baseline in step 52. Any time there is a change in one of the baseline patterns for an authorized user, it is considered an outlier and administrators are alerted in step 54 and the audit log is flagged in step 56 through the notification engine 46.

Figure 4:
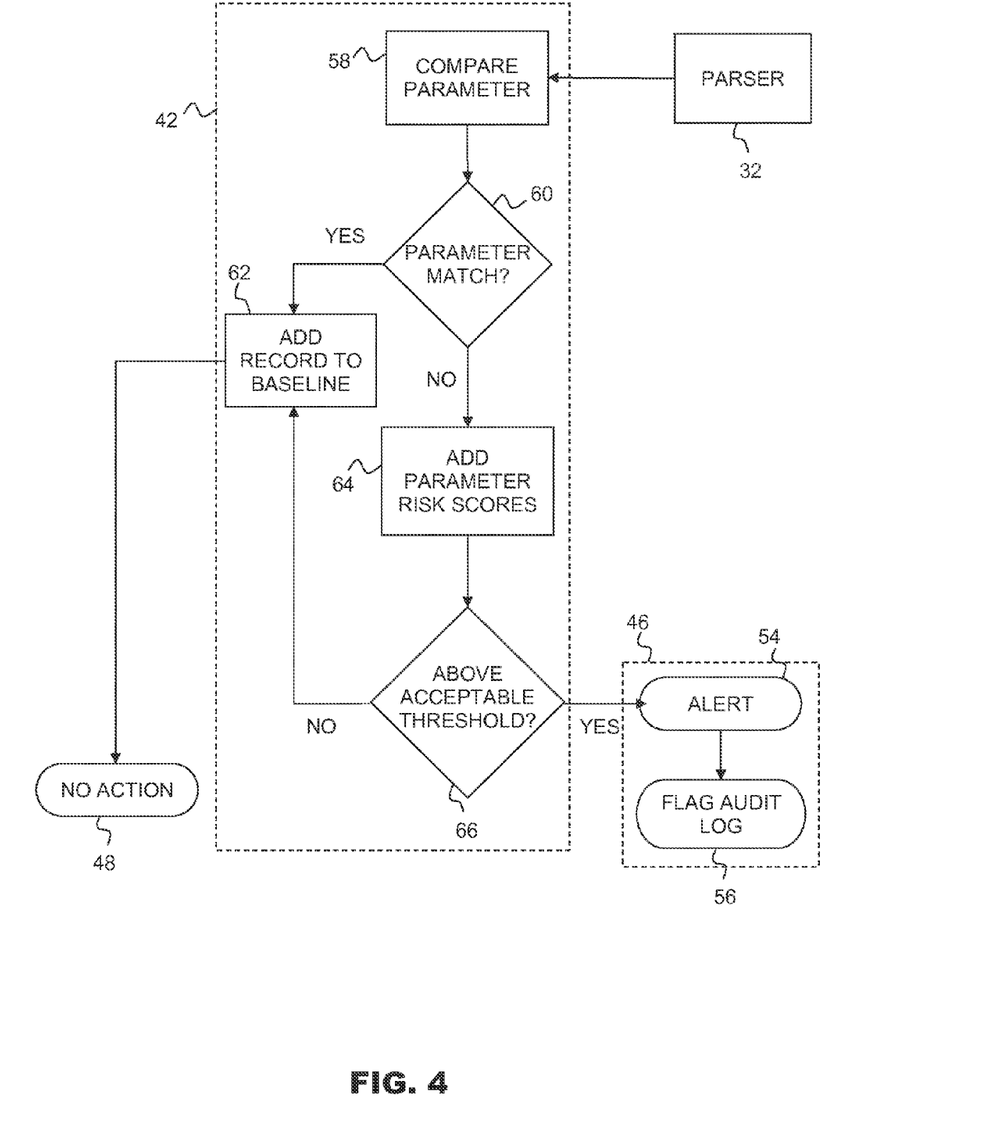
FIG. 4 is a simplified logical flow diagram of a pattern analyzer.

If the authorized user is known, the data will be sent directly to the pattern analyzer in step 42. The pattern analyzer in step 42 maintains a baseline for each unique authorized user that accesses systems at a healthcare facility.

FIG. 4 illustrates the pattern analyzer of step 42. The normalized data is also compared to the baseline for the authorized user that generated the audit log in step 58. Each parameter of the audit log data is checked against existing usage parameter patterns, the baseline, for that authorized user for a match in step 60. Parameter matches are scored and these risk scores are added together in step 64. The cumulative score of matching parameters is compared to a risk threshold in step 66. If most parameters match in step 60, the score will be low because there are few outliers. If the score does not exceed the risk threshold in step 66, the record is added to the baseline for that authorized user in step 62. This allows the baseline of each authorized user to be up-to-date on any changes in an authorized user's schedule. If all parameters match in step 60, the risk score is zero. If fewer parameters match in step 60, then risk level is considered high and a higher score is assigned. With a high score that is in excess of the risk threshold in step 66, an alert will be sent to administrators in step 54 and the audit log will be flagged for further review in step 56 through the notification engine 46.

In an alternative embodiment, each parameter can have a weighted risk score, so parameter outliers that may be a higher cause for concern exceed the threshold and are immediately reported in step 54 through the notification engine 46.

Figure 5:
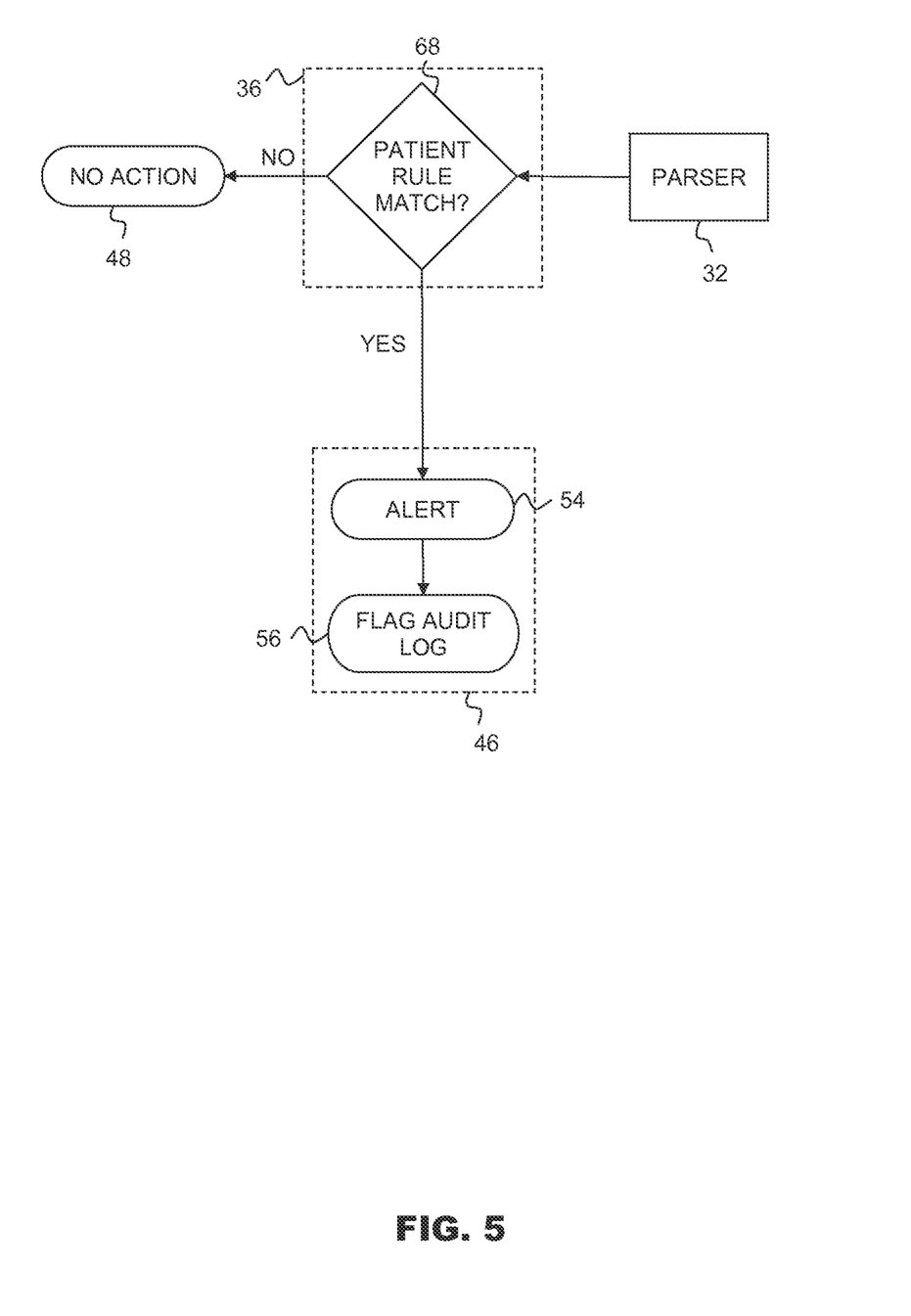
FIG. 5 is a simplified logical flow diagram of a patient rules engine.

FIG. 5 illustrates the patient rules engine of step 36. The normalized data is also checked for against a set of patient rules to see if there are any matches in step 68. Patient rules are made up of a list of patients, such as VIP's, privacy conscious, movie stars, football players, etc., so an alert in step 54, through the notification engine 46, may be generated when the listed patient's PHI is accessed. This list of patient-specific rules may be updated by administrators. If the data matches a patient rule in step 68, an alert 54 is created through the notification engine 46 and the audit log is flagged in step 56. If no match is found in patient rule match of step 68, then no action is taken in step 58.

In an alternative embodiment, the patient rules engine of step 36 will only find a patient rule match in step 68 if that patient is in the healthcare facility.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for detecting privacy violations of patient personal healthcare information (PHI) access comprising:
at least one processor defining part of a privacy detection system performing the steps of:
generating an audit log for an access to PHI by an authorized user with the at least one processor;
communicating with at least one system to collect the audit log with the at least one processor;
normalizing and parsing the audit log into a predefined and uniform data format with the at least one processor;
discarding parameters considered to be irrelevant to a risk of privacy violation with the at least one processor;
comparing at least one parameter of the audit log to a corresponding baseline parameter range of an access to PHI by an authorized user considered to be normal and non-healthcare authorized user information with the at least one processor;
adding a weighted risk score assigned to the corresponding baseline parameter range to a cumulative risk score for the access to PHI by the authorized user if the parameter of the audit log differs from the corresponding baseline parameter range with the at least one processor;
creating an alert and flagging the audit log when the cumulative risk score exceeds an acceptable threshold with the at least one processor;
storing the normalized and parsed audit log in a storage database with the at least one processor;
comparing the audit log to a set of patient rules with the at least one processor; and
creating the alert and flagging the audit log when at least one audit log parameter matches a corresponding parameter of the set of patient rules with the at least one processor.

2. The method of claim 1 further comprising:
combining the parameters of the audit log to the baseline parameters for the authorized user when the cumulative risk score is under the acceptable threshold.

3. The method of claim 1 including a learning engine routine further comprising:
creating and storing a new set of baseline parameters when the audit log is generated by an unknown user;
combining the audit log to the baseline parameters for the unknown user for a predefined amount of time; and
creating the alert in response to detection of an unknown user.

4. The method of claim 1 further comprising:
combining the audit log to the baseline parameters for an unknown user until an administrator identifies the baseline parameters for the unknown user as normal.

5. A method for detecting privacy violations of patient personal healthcare information (PHI) access comprising:
at least one processor defining part of a privacy detection system performing the steps of:
generating an audit log when an access to PHI by an authorized user occurs with the at least one processor;
normalizing and parsing the audit log into a predefined and uniform data format with the at least one processor;
discarding parameters considered to be irrelevant to a risk of privacy violation with the at least one processor;
comparing at least one parameter of the audit log to a corresponding baseline parameter range of the authorized user and non-healthcare authorized user information with the at least one processor;
adding a weighted risk score assigned to the baseline parameter range to a cumulative risk score for the access to PHI by the authorized user, if the parameter of the audit log differs from the corresponding baseline parameter range for the authorized user with the at least one processor;
creating an alert and flagging the audit log when the cumulative risk score exceeds an acceptable threshold with the at least one processor;
storing the normalized and parsed audit log in a storage database with the at least one processor;
creating the alert and flagging the audit log when at least one audit log parameter matches a corresponding parameter of a set of patient rules with the at least one processor;

combining the audit log to the baseline parameter range for the authorized user when the cumulative risk score is under the acceptable threshold with the at least one processor; and creating an alert when an unknown user generated the audit log and storing the audit log as the baseline parameter range for the unknown user with the at least one processor.

* * * * *